United States Patent [19]

Frey

[11] Patent Number: 5,549,645
[45] Date of Patent: Aug. 27, 1996

[54] PERITONEAL DIALYSIS CATHETER CLIP AND METHOD

[76] Inventor: James R. Frey, 1490 S. Clinton St., Defiance, Ohio 43512

[21] Appl. No.: 375,475

[22] Filed: Jan. 19, 1995

[51] Int. Cl.⁶ ..................................... A61M 1/00
[52] U.S. Cl. .............. 604/29; 604/174; 604/179
[58] Field of Search ............ 604/29, 174, 179, 604/283; 128/207.17, 207.18, DIG. 6, DIG. 26

[56] References Cited

U.S. PATENT DOCUMENTS

| | | | |
|---|---|---|---|
| 4,230,110 | 10/1980 | Beroff | 604/174 |
| 4,632,670 | 12/1986 | Mueller, Jr. | 604/174 |
| 4,838,255 | 6/1989 | Lambert | 128/202.16 |
| 4,895,570 | 1/1990 | Larkin | 604/411 |
| 4,915,104 | 4/1990 | Marcy | 128/207.18 |
| 4,995,384 | 2/1991 | Keeling | 128/207.18 |
| 5,137,524 | 8/1992 | Lynn et al. | 604/283 |
| 5,146,913 | 9/1952 | Khorsandian et al. | 128/200.26 |
| 5,222,486 | 6/1993 | Vaughn et al. | 128/200.24 |
| 5,233,979 | 8/1993 | Strickland | 128/207.14 |
| 5,237,988 | 8/1993 | McNeese | 128/207.17 |
| 5,243,971 | 9/1993 | Sullivan et al. | 128/207.18 |
| 5,305,742 | 4/1994 | Styers et al. | 128/207.17 |

*Primary Examiner*—Randall L. Green
*Assistant Examiner*—Laird J. Knights
*Attorney, Agent, or Firm*—Willian Brinks Hofer Gilson & Lione

[57] ABSTRACT

The present invention relates to a device for securing the terminal end of a catheter extension (300) used by a peritoneal dialysis patient. The Cosentino Peritoneal Dialysis Catheter Clip (3CDP) (100) consists of a rigid plastic body (100) open at both the proximal end (101) and distal end (102). Attached to the distal end (102) of the 3CPD (100) is a neck cord (120) which is simultaneously threaded through a pair of holes (112) in the distal end (102) of the 3CPD (100) and through a neck cord adjustor (200) housed inside the distal end (102) of plastic body (101). The adjustor assembly (200) is a push button arrangement made up of a push button shell (210), a push button (220), and a spring (230). The neck cord (120), which is threaded through neck cord adjustor passage (223), is pinched via the spring action of the push button (220) and the neck cord length is maintained. When a length adjustment is necessary, the wearer need only tug gently on the loose ends of the neck cord (120), pulling the neck cord (120) through the neck cord adjustor (200). The push button (220) need not be depressed to adjust the neck cord length. The neck cord (120) is worn over the head and around the neck of the patient like a necklace. The proximal end (101) of the 3CPD (100) is then slipped over the terminal end of the catheter extension (300) such that the body (110) snaps into place, covering the catheter nozzle safety cap (310). Prior to attaching the 3CPD (100) to the terminal end of the catheter (300), a small disposable latex finger cot may be slipped over the safety cap (310) to maintain aseptic conditions. An additional set of holes (111) can be found near the proximal end (101) of the body (110). The diameter of the proximal end (101) is slightly larger than the diameter of the distal end (102) so that the 3CPD (100) can be reversed accommodate catheter extensions (300) having different sized safety caps (310).

17 Claims, 2 Drawing Sheets

PERITONEAL DIALYSIS CATHETER CLIP AND METHOD

FIELD OF THE INVENTION

The present invention relates to the medical treatment field of peritoneal dialysis. More specifically, the present invention relates to a lightweight, inexpensive clip device to secure the terminal end of a catheter extension used by many dialysis patients when not connected to the dialysis machine.

BACKGROUND OF THE INVENTION

Peritoneal dialysis is a common mode of kidney dialysis for treatment of many forms of renal ailments (peritoneal dialysis should not be confused with renal or hemodialysis, a process where the blood of a patient is removed, filtered to eliminate waste products, and then returned to the patient). Peritoneal dialysis patients connect a semi-permanent catheter, usually located in the abdomen, to a remote source of a dialysate. Dialysate, normally a glucose-water solution, is infused into the peritoneal cavity via a catheter extension and catheter. Waste products diffuse through the peritoneal membrane and are absorbed by the dialysate which is then drained from the peritoneal cavity, carrying the waste products from the patient's system. The infusion and removal of dialysate is referred to as an exchange. Exchanges are repeated as often as necessary to reduce the impurities in the blood of the patient. These exchanges can be performed either manually or by machine.

Because a peritoneal dialysis patient must perform numerous exchanges in a relatively short period of time, a semi-permanent catheter is installed into the abdomen of the patient. The catheter is taped into placed to the abdomen of the patient to reduce movement of the catheter near the entry site, aka catheter tunnel. The catheter and the catheter extension (which consists of a catheter connector, a length of tubing, a flow control valve, a nozzle, and a safety cap) is then available for repeated connections to the dialysate source via the catheter extension. Without the semi-permanent catheter, a patient would be forced to endure repeated insertions of a temporary catheter each time an exchange was to be performed, causing pain from and possible infection of many small puncture wounds.

When the dialysis system is not in use (that is, when the patient is between exchanges), the unwieldy catheter extension dangles freely from the catheter tunnel site, becoming a nuisance at best, and a possible health hazard at worst. A dangling catheter extension can irritate the catheter tunnel, possibly causing infection, and can interfere with activities for which the patient needs both hands free.

The solution most commonly employed to eliminate the dangling catheter extension problem is a pouch which encircles the waist of the patient similar to the currently popular "fanny pack" used for carrying loose articles. The terminal end of the catheter extension (that is, the end which is connected to the dialysate source) rests in the pouch while not in use. Unfortunately, the pouch is not very comfortable, since securing the pouch to avoid slippage requires tightening of the straps around the waist. Further, the pouch is not very adaptable, since it's vertical position on the wearer's body is almost completely unadjustable. Finally, the pouch is not very convenient, since it is usually made of fabric, which absorbs water during normal activities such as a bath or shower, and then takes an inordinate amount of time to dry.

SUMMARY OF THE INVENTION

A Cosentino Peritoneal Dialysis Catheter Clip (3CPD) is a medical device designed to eliminate the above-mentioned problems which peritoneal dialysis patients face every day. The 3CPD is a convenient, comfortable, and inexpensive device for securing the terminal end of the catheter extension when not in use.

The preferred embodiment of the 3CPD consists of a rigid plastic cylindrical body, preferably made by the injection molding process. The body has a generally circular cross section and is open at both the proximal end (that is, the end closer to the terminal end of a catheter extension safety cap) and the distal end (the end farther from the terminal end of a catheter extension safety cap). Two U-shaped grooves are located at each end, with the grooves at each end being positioned opposite each other, with respect to the circumference of the body. The 3CPD has a pair of holes in the body near the distal end, the holes being located opposite each other. The holes receive an adjustable neck cord.

The adjustable neck cord, which is preferably made of nylon or some other non-absorbent material capable of use in a wet environment such as a bath or shower, is threaded through the pair of holes in the distal end of the 3CPD body. The cord length is fixed by a neck cord adjustor assembly which consists of a spring-loaded push button arrangement fitted partially inside the distal end of the cylindrical body. The neck cord adjustor assembly also has a passage therethrough. When properly nested inside the 3CPD body, the holes in the adjustor assembly align with the holes in the 3CPD body, thus allowing the neck cord to be threaded through the two simultaneously. A small spring inside the adjustor assembly provides the necessary biasing force to "pinch" the neck cord, thus maintaining the length of the neck cord and preventing it from slipping. The adjustor assembly is not permanently affixed to the 3CDP body, but is allowed to "float" freely with the body, and is actually kept in place by the neck cord itself.

Additionally, an identical set of holes is located near the proximal end of the body, giving the 3CDP a reversible option. The diameter of the proximal end of the body is slightly larger than the diameter of the distal end. To secure the terminal end of a catheter extension having a safety cap of a different size, the wearer need only unthread the neck cord from the pair of holes at the distal end, remove the neck cord adjustor, rotate the 3CDP 180 degrees about its transverse axis, insert the adjustor assembly into the proximal end, and re-thread the neck cord in the alternate pair of holes. Thus, the 3CPD is reversed and ready to secure the terminal end of a catheter extension having a smaller safety cap.

Accordingly, it is an object of the present invention to provide a lightweight, inexpensive, yet reliable catheter extension clip to secure the terminal end of a catheter extension when not in use by a peritoneal dialysis patient.

It is further an object of the present invention to provide a lightweight, inexpensive, yet reliable catheter extension clip having a fully adjustable neck cord which allows the invention to be adapted to various situations.

It is yet further an object of the present invention to provide a lightweight, inexpensive, yet reliable catheter extension clip which can accommodate several different sizes of catheter extension safety caps.

For a further understanding of the present invention and the objects thereof, attention is directed to the drawings and the following brief description thereof, to the detailed

DETAILED DESCRIPTION OF THE PREFERRED EMBODIMENT

Figure 1:
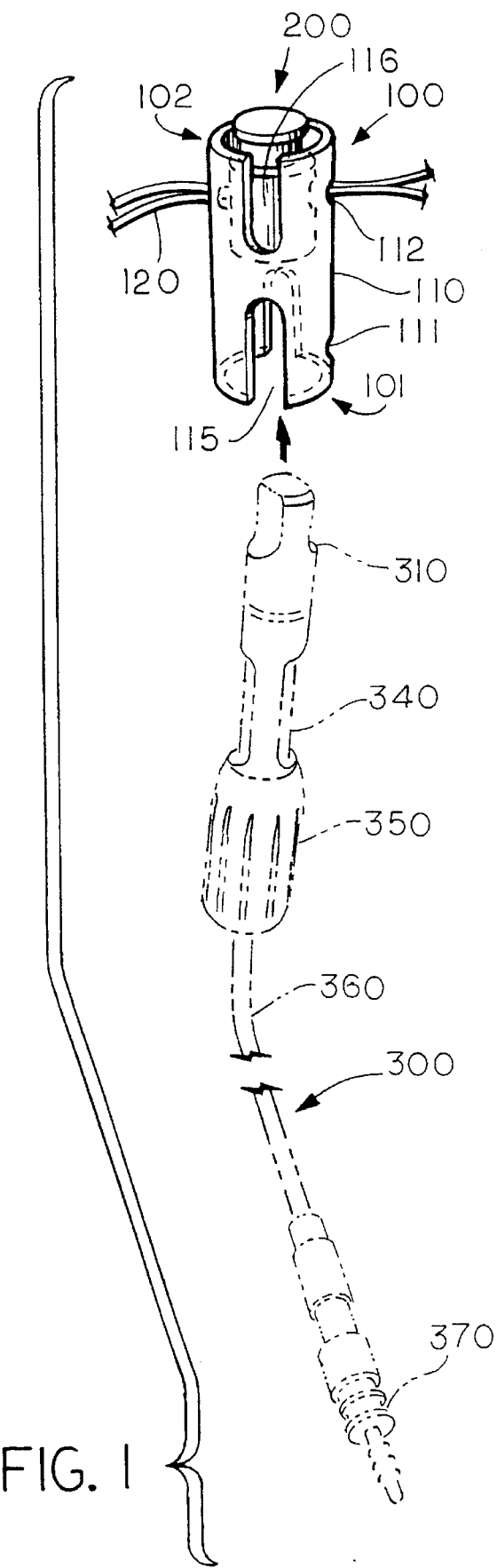
FIG. 1 is a perspective view of the preferred embodiment of a catheter clip of the present invention along with a typical catheter extension (shown in phantom) to which it attaches.
Figure 2:
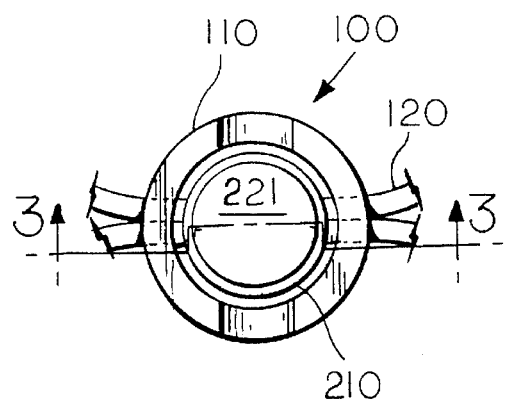
FIG. 2 is a top plan view of the catheter clip of FIG. 1.
Figure 3:
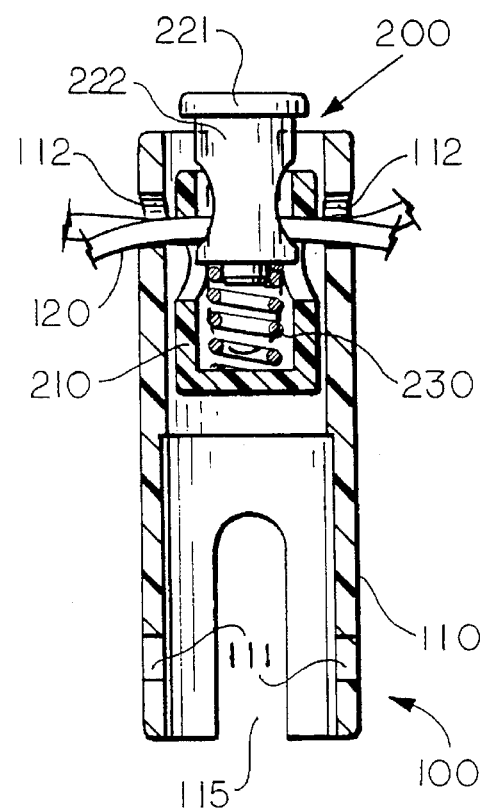
FIG. 3 is an elevational view partly in cross section of the catheter clip of FIGS. 1 and 2.
Figure 4:
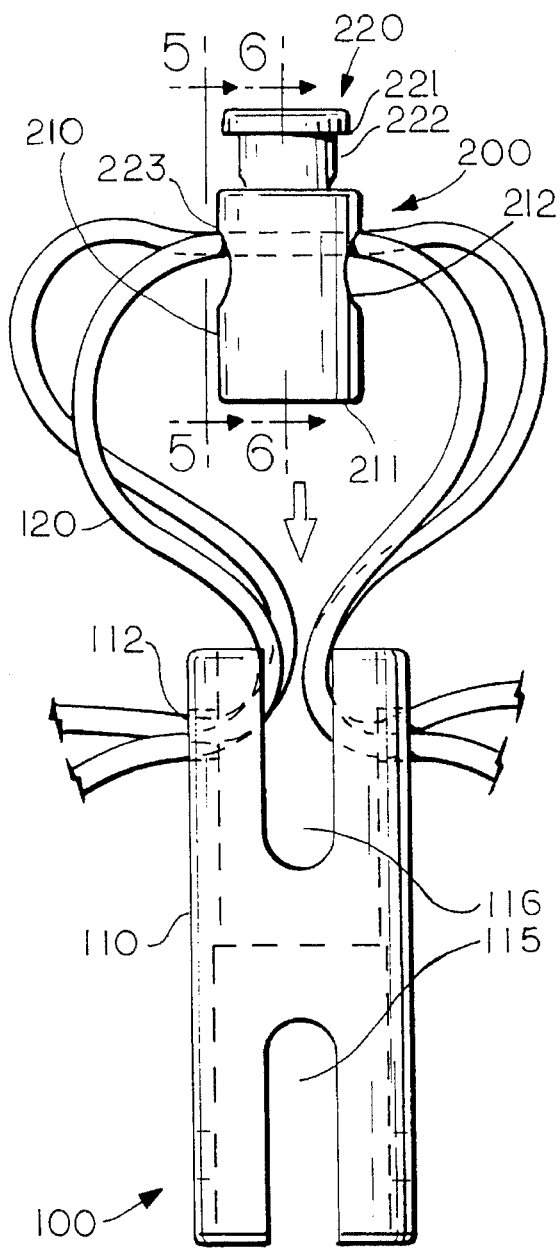
FIG. 4 is an elevational view of the catheter clip of FIGS. 1-3 with the neck cord adjustor assembly partially removed.

The 3CDP 100, shown in FIGS. 1-4, consists of rigid, cylindrical, hollow body 110 having proximal end 101 and distal end 102. Its thin walls are preferably made of injected molded plastic, or the equivalent, to achieve durable, lightweight, and cost effective qualities. Formed into body 110 are U-shaped slots 115 and 116, such that two slots 115 of equal size are located at proximal end 101 and are spaced opposite each other, as best shown in FIGS. 1 and 4, and two slots 116 of equal size are located at distal end 102 and are spaced opposite each other, also best shown in FIGS. 1 and 4. The diameters of proximal end 101 and distal end 102 are slightly different, for reasons to be discussed later in the specification. Also contained in body 110 are two holes 111 and two holes 112, located near proximal and distal ends 115 and 116, respectively. Holes 111 are located near proximal end 101 and are spaced opposite each other. Likewise, holes 112 are located near distal end 102 and are also spaced opposite each other, as shown in FIGS. 1 and 3.

Figure 5:
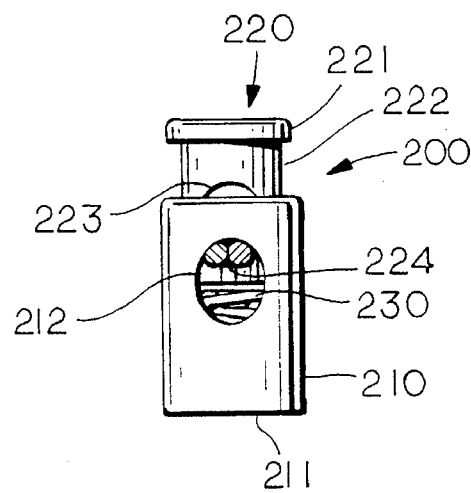
FIG. 5 is an elevational view of the neck cord adjustor assembly of the catheter clip of FIGS. 1-4.
Figure 6:
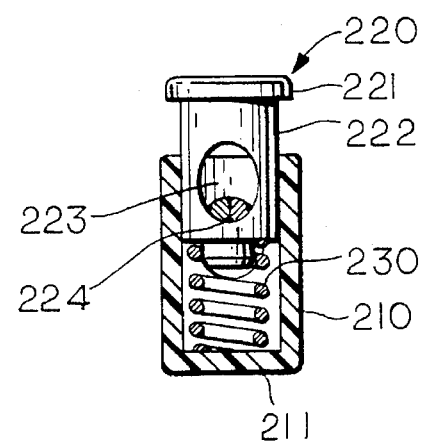
FIG. 6 is an elevational view partly in cross section of the neck cord adjustor assembly of the catheter clip of FIGS. 1-4.

A key element in the operation of the present invention is neck cord adjustor assembly 200 (best shown in FIGS. 5 and 6). Adjustor assembly 200 consists of push button shell 210 having a bottom 211 and two openings 212 positioned opposite each other. Slidably positioned inside adjustor body 210 is push button 220 which consists of push button face 221, push button shaft 222, and push button catches 224. Push button passage 223 extends completely through push button shaft 222 and is generally perpendicular to the longitudinal axis of push button shaft 222. Spring 230 provides the biasing force to urge push button 220 away from bottom 211 of adjustor body 210. Push button catches 224 found on push button shaft 222 prevent push button 220 from completely exiting adjustor body 210.

Adjustor assembly 200 is positioned inside either proximal end 101 or distal end 102, depending upon which size catheter extension 300 is in use (at present, the lion's share of the catheter extension market is owned by Baxter Medical Products; their extensions are sold with two differently sized safety caps only: a large size for patients who are "fine motor skill impaired" and a smaller size for those who are not). In the preferred embodiment of the present invention, proximal end 101 is sized to fit the larger safety cap, and distal end 102 is sized to fit the smaller safety cap. The outer diameter of neck cord adjustor assembly 210 is slightly smaller than the inner diameter of distal end 102 so that the adjustor assembly can fit loosely inside either proximal end 101 or distal end 102 of body 110. When adjustor assembly 200 is properly positioned inside 3CPD body 110, passage 223 of push button shaft 222 aligns with openings 212 of push button shell 210, which align with either holes 115 in proximal end 101 or holes 116 in distal end 102, depending upon which end is chosen to secure the terminal end of catheter extension 300.

Having properly positioned adjustor assembly 200 partially inside 3CPD body 110, neck cord 120 is threaded simultaneously through openings 212 of adjustor body 210, passage 223 of push button shaft 222, and either holes 115 or 116. The biasing force of spring 230 urges push button 220 up and away from bottom 211 and pinches neck cord 120 such that the length of neck cord 120 is maintained. Push button catches 224 prevent push button 220 from completely exiting push button shell 210 by catching on the upper edges of push button shell openings 212.

Shown in FIG. 1 (in phantom) is typical catheter extension 300 to which catheter clip 100 attaches. Catheter connector 370 which is attached to catheter cannula (not shown) is connected to catheter extension tubing 360, which in turn is connected to flow control valve 350. Flow control valve 350 is attached to catheter extension body 340 which is finally connected to a catheter extension nozzle (not shown) which establishes fluid communication with a dialysate source (not shown) during the performance of exchanges. The catheter extension nozzle is protected by safety cap 310.

The mode of operation is simple. When the peritoneal dialysis patient is finished with an exchange, he or she simply twists flow control valve 350 to the "off" position and screws safety cap 310 onto catheter extension body 340 to protect catheter extension nozzle (not shown) from contaminants. A small disposable latex finger cot (not shown) may then be slipped over safety cap/catheter extension body 310/340 to further maintain aseptic conditions. The patient inserts safety cap 310 into proximal end 101 or distal end 102 of 3CPD body 110 (depending upon the size of safety cap 310) until safety cap 310 snaps into place. The patient is then free to proceed with normal activities with the terminal end of catheter extension 300 secured and out of the way.

After attaching 3CPD 100 to safety cap 310 of catheter extension 300, the length of neck cord 120 may be easily adjusted. The biasing force of spring 230 is not so great as to totally prevent neck cord 120 from sliding. To adjust the length of neck cord 120, push button 220 need not be depressed; the patient need only gently tug on opposing strands of neck cord 120 and it will slide through passage 223, openings 212, and holes 115 or 116, thus shortening or lengthening neck cord 120 as desired.

Although the best mode contemplated by the inventor for carrying out the present invention as of the filing date hereof has been shown and described herein, it will be apparent to those skilled in the art that suitable modifications, variations, and equivalents may be made without departing from the scope of the invention, such scope being limited solely by the terms of the following claims.

What is claimed is:

1. A device for securing the terminal end of a catheter extension used in peritoneal dialysis treatment, said device comprising, a generally hollow body, said body having a proximal end and a distal end, each of said proximal end and said distal end being open, said generally hollow body having a first set of holes, said first set of holes being located near said proximal end of said generally hollow body, said first set of holes being spaced evenly apart, and said generally hollow body also having a second set of holes, said second set of holes being located near said distal end of said generally hollow body, said second set of holes being spaced evenly apart;

a neck cord, said neck cord being threaded through one of said first set and said second set of holes; and, means for adjusting the vertical position of said device with respect to the body of the wearer, said adjusting means clamping onto said neck cord.

2. A device according to claim 1 wherein said means for adjusting said vertical position of said device comprises a push button assembly.

3. A device according to claim 2 wherein said push button assembly comprises:

a push button shell, said shell having at least one side wall, an open top and a closed bottom, said shell having a set of openings in said at least one side wall, one of said openings of said set being positioned opposite the other of said openings of said set;

a push button, said push button comprising a push button shaft and a push button face, said push button being positioned partially within said push button shell, said push button being slidable with respect to said push button shell, said push button shaft having a passage therethrough such that the longitudinal axis of said passage extends generally perpendicularly to the longitudinal axis of said push button shaft;

a spring, said spring located between said push button shell bottom and said push button shaft; and, a push button catch, said push button catch preventing said push button from exiting said push button shell due to the biasing force of said spring.

4. A device according to claim 3 wherein said generally hollow body and said push button assembly are both cylindrical, said generally hollow body and said push button assembly each having a circular cross section.

5. A device according to claim 4 wherein said generally hollow body comprises a thin wall of material, said thin wall having a plurality of U-shaped slots at each of said distal end and said proximal end.

6. A device according to claim 5 wherein said U-shaped slots in said proximal end are spaced evenly apart around said proximal end, and said U-shaped slots in said distal end are spaced evenly around said distal end.

7. A device according to claim 6 wherein the diameter of said proximal end is larger than the diameter of said distal end, whereby enabling said device to secure catheter extensions of differing diameters.

8. A device according to claim 7 wherein said generally hollow body is constructed of an injected molded plastic material.

9. A device according to claim 8 wherein said neck cord comprises a generally non-absorbent material such as nylon.

10. A device for securing the terminal end of a catheter extension, said device comprising:

an elongate rigid tube, said tube comprising a cylindrical wall, a top and a bottom, said top and said bottom being open, said cylindrical wall having a first set of holes near said top of said tube, and a second set of holes near said bottom of said tube, one of said first set of holes being spaced opposite the other of said first set of holes, one of said second set of holes being spaced opposite the other of said second set of holes;

a neck cord, said neck cord being threaded through said first set of holes near said top of said tube; and, means for adjusting said neck cord, said means for adjusting said neck cord being located partially within said top of said tube.

11. A device according to claim 10 wherein said means for adjusting said neck cord comprises a push button assembly, said push button assembly comprising:

a push button shell, said shell having a cylindrical side wall, an open top and a closed bottom, said shell also having a set of openings in said cylindrical side wall, one of said openings being positioned opposite the other of said openings;

a push button, said push button being slidable with respect to said push button shell, said push button comprising a push button shaft and a push button face, said push button being positioned partially within said push button shell, said push button shaft having a passage therethrough such that the longitudinal axis of said passage extends generally perpendicularly to the longitudinal axis of said push button shaft;

a spring, said spring located between said push button shell bottom and said push button shaft; and, a push button catch, said push button catch preventing said push button from exiting said push button shell due to the biasing force of said spring.

12. A device according to claim 11 wherein the diameter of said top of said tube measures slightly smaller than the diameter of said bottom of said tube.

13. A device according to claim 12 wherein said tube is reversible, such that when rotated 180 degrees about its transverse axis, said top serves as said bottom and said bottom serves as said top.

14. A method of securing the terminal end of a catheter extension, said method comprising the steps of:

providing a catheter clip, said clip comprising a generally hollow body, said body having a cylindrical side wall, an open proximal end and an open distal end, said cylindrical side wall having a first set of holes located near said proximal end, one of said first set of holes being spaced opposite the other of said first set of holes;

providing a neck cord; and, providing means for clamping said neck cord, said means for clamping said neck cord effectively adjusting the vertical position of said device with respect to the wearer, said means for clamping said neck cord comprising:

a push button assembly, said push button assembly comprising a push button shell, said shell having a cylindrical side wall, an open top and a closed bottom, said shell also having a set of openings in said cylindrical side wall, one of said set of openings being positioned opposite the other of said set of openings;

a push button, said push button being slidable with respect to said push button shell, said push button comprising a push button shaft and a push button face, said push button being positioned partially within said push button shell, said push button shaft having a passage therethrough such that the longitudinal axis of said passage extends generally perpendicularly to the longitudinal axis of said push button shaft;

a spring, said spring located between said push button shell bottom and said push button shaft; and, a push button catch, said push button catch preventing said push button from exiting said push button shell due to the biasing force of said spring.

15. The method according to claim 14 wherein said first set of holes, said push button shell openings, and said push button shaft passage all align to receive said neck cord.

16. The method according to claim 15 wherein said distal end contains a second set of holes, each of said second set of holes being spaced evenly apart.

17. The method according to claim 16 wherein said generally hollow body is reversible such that when said generally hollow body is rotated 180 degrees about its transverse axis, said means for clamping said neck cord can be partially inserted into said proximal end whereby aligning said second set of holes, said push button shell openings, and said push button shaft passage to receive said neck cord.

* * * * *